US012655476B2

(12) United States Patent  
Halterman

(10) Patent No.: US 12,655,476 B2  
(45) Date of Patent: Jun. 16, 2026

(54) METHOD OF RAPID EXTRACTION OF DNA FROM SALIVA AND qPCR AMPLIFICATION OF GROUP A STREPTOCOCCUS DNA

(71) Applicant: SalivIQ Diagnostics Inc., Harrisonburg, VA (US)

(72) Inventor: Julia A. Halterman, Harrisonburg, VA (US)

(73) Assignee: SalivIQ Diagnostics, Inc., Harrisonburg, VA (US)

( * ) Notice: Subject to any disclaimer, the term of this patent is extended or adjusted under 35 U.S.C. 154(b) by 0 days.

(21) Appl. No.: 19/306,722

(22) Filed: Aug. 21, 2025

(65) Prior Publication Data

US 2025/0376722 A1 Dec. 11, 2025

Related U.S. Application Data

(63) Continuation of application No. PCT/US2025/010203, filed on Jan. 3, 2025.

(60) Provisional application No. 63/553,210, filed on Feb. 14, 2024.

(51) Int. Cl.

| | |
|---|---|
| *C12Q 1/6851* | (2018.01) |
| *C12Q 1/48* | (2006.01) |
| *C12Q 1/6806* | (2018.01) |
| *C12Q 1/6809* | (2018.01) |
| *C12Q 1/6848* | (2018.01) |
| *C12Q 1/686* | (2018.01) |
| *C12Q 1/689* | (2018.01) |
| *C12Q 1/70* | (2006.01) |

(52) U.S. Cl.

CPC ............. *C12Q 1/6851* (2013.01); *C12Q 1/48* (2013.01); *C12Q 1/6806* (2013.01); *C12Q 1/6809* (2013.01); *C12Q 1/6848* (2013.01); *C12Q 1/686* (2013.01); *C12Q 1/689* (2013.01); *C12Q 1/70* (2013.01); *C12Y 207/07* (2013.01)

(58) Field of Classification Search

CPC ...... C12Q 1/6851; C12Q 1/48; C12Q 1/6806; C12Q 1/6809; C12Q 1/6848; C12Q 1/686; C12Q 1/689; C12Q 1/70; C12Y 207/07

See application file for complete search history.

(56) References Cited

U.S. PATENT DOCUMENTS

| | | | | |
|---|---|---|---|---|
| 2017/0327875 A1* | 11/2017 | Duan | ..................... | C12Q 1/689 |
| 2021/0262025 A1 | 8/2021 | Bhatia et al. | | |

FOREIGN PATENT DOCUMENTS

| | | | | |
|---|---|---|---|---|
| CN | 106282322 | * | 1/2017 | |
| CN | 106282322 A | * | 1/2017 | ............. C12Q 1/689 |

OTHER PUBLICATIONS

Sweet et al., Forensic Science International Inc., vol. 83, pp. 167-177, (Year: 1996).*  
Dreskin et al., Bulletin 3318, pp. 1-6, (Year: 2022).*  
International Search Report and Written Opinion of the International Searching Authority dated Mar. 13, 2025, issued in PCT/US2025/010203.  
Peachey et al., "Use of saliva-based qPCR diagnostics for the accurate, rapid, and inexpensive detection of strep throat." Diagnosis. Jan. 5, 2024. vol. 11, No. 2, pp. 178-185.  
GenBank Accession No. MT815454, "*Streptococcus pyogenes* isolate 75P exotoxin B (speB) gene, partial cds", Mar. 8, 2022 [online]. Retrieved from https://www.ncbi.nlm.nih.gov/nuccore/MT815454.1/ on Aug. 18, 2025.

* cited by examiner

*Primary Examiner* — Cynthia B Wilder  
(74) *Attorney, Agent, or Firm* — Womble Bond Dickinson (US) LLP

(57) ABSTRACT

A method for processing a saliva sample for downstream DNA analysis. The method includes mixing the saliva sample with a chelating resin solution to form a mixture, incubating the mixture at a temperature of 120° C. or lower and duration of at least 1 minute, wherein the temperature and duration are inversely related, shaking the mixture before and after incubation for a period ranging from 0 seconds to 2 hours, separating the mixture into a supernatant and a sedimented chelating resin using either centrifugation or by allowing natural gravitational settling, and recovering the supernatant for subsequent analysis.

20 Claims, 5 Drawing Sheets

Specification includes a Sequence Listing.

SEQUENCE LISTING

```
Sequence total quantity: 2
SEQ ID NO: 1             moltype = DNA  length = 22
FEATURE                  Location/Qualifiers
source                   1..22
                         mol_type = genomic DNA
                         organism = Streptococcus pyogenes
SEQUENCE: 1
aaagtaggcg gacatgcctt tg                                          22

SEQ ID NO: 2             moltype = DNA  length = 21
FEATURE                  Location/Qualifiers
source                   1..21
                         mol_type = genomic DNA
                         organism = Streptococcus pyogenes
SEQUENCE: 2
caagacggaa gaagccgtca g                                           21
```

METHOD OF RAPID EXTRACTION OF DNA FROM SALIVA AND qPCR AMPLIFICATION OF GROUP A *STREPTOCOCCUS* DNA

CROSS-REFERENCE TO RELATED APPLICATIONS

The present application is a continuation of International Application No. PCT/US2025/010203, filed on Jan. 3, 2025, and claims the benefit of U.S. Provisional Patent Application No. 63/553,210, filed on Feb. 14, 2024, which are hereby incorporated by reference for all purposes as if fully set forth herein.

INCORPORATION BY REFERENCE

A sequence listing containing the nucleotide and/or amino acid sequences disclosed in the present application is submitted in the form of an XML file entitled 2025-08-21_SAL002_DNA_Sequences.xml, created on Jan. 3, 2025, and is 3,000 bytes in size, which is incorporated by reference for all purposes as if fully set forth herein.

BACKGROUND

Field

Exemplary embodiments relate to medical diagnostic methods. In particular, exemplary embodiments relate to methods of rapid extraction of deoxyribonucleic acid (DNA) from saliva and quantitative polymerase chain reaction (qPCR) amplification of Group A *Streptococcus* (GAS) DNA for the diagnosis of strep throat infection.

Discussion of the Background

Antibiotic resistance is a global public health concern, and the World Health Organization urges countries to take action against this threat at the national, regional, and local level. In the United States alone over one million patients are being improperly prescribed antibiotics for pharyngitis each year due to the inaccuracy of rapid *Streptococcus pyogenes* (*Streptococcus pyogenes* is commonly known as Group A *Streptococcus,* referred to herein as GAS, "strep throat", or ST) tests. The United States National Action Plan for Combating Antibiotic-Resistant Bacteria calls for the development and validation of new diagnostics to rapidly distinguish between viral and bacterial pathogens and for these diagnostics to be easily implemented. In addition, the Centers for Disease Control and Prevention calls for improvement of antibiotic prescribing to minimize missed and delayed diagnoses, placing viral pharyngitis and ST as top priority conditions.

Outpatient health care facilities were responsible for prescribing approximately 269 million antibiotic prescriptions in 2015, and it was estimated that 30% of those prescriptions were inappropriate. Pharyngitis is commonly diagnosed in outpatient settings and is the third top diagnosis for which antibiotics are prescribed. In adults with pharyngitis, 10% have ST, the only form of pharyngitis requiring antibiotics. However, approximately 60% of adults with pharyngitis are prescribed antibiotics. These statistics highlight the pervasiveness of the inappropriate prescribing of antibiotics for pharyngitis and suggest that antibiotics are being prescribed even with a negative ST diagnostic result.

Outpatient health care facilities may currently utilize rapid antigen detection tests (RADT) for ST, but those screening procedures often yield a high rate of false negative results. The most common RADT is the lateral flow immunoassay, whereby antibodies detect GAS cell wall antigens from throat swab samples. A 2014 meta-analysis analyzing 48 studies found that the sensitivity (true-positive rate) of ST RADTs averaged 86% (with lateral flow immunoassays ranging from 59-96% sensitivity) and the specificity (true-negative rate) averaged 96%. Therefore, many false negative diagnoses can occur, depending on the brand of RADT used and the proficiency of those performing the test.

It is considered a best practice to verify a negative RADT diagnosis with a reference standard beta-hemolytic GAS culture; however, this may take 24-72 hours to grow and is an additional cost, so many clinics do not perform this secondary test. Unfortunately, a false negative result can be detrimental to patient health in that it can delay recovery and can lead to further complications when antibiotics are not prescribed. In one study, 42% of patients with a false negative RADT diagnosis had moderate to heavy bacterial burden, and more than 4% suffered from severe complications associated with untreated ST.

Although widespread use of the ST RADT has reduced the overall number of antibiotic prescriptions for pharyngitis, and average ST RADT specificity is relatively high, specificity for these tests can still range from 78-100%. This can result in false positive diagnoses, which further contributes to the unnecessary prescription of antibiotics. Altogether, there is great need for more sensitive and specific ST diagnostic tools in outpatient settings.

One of the most sensitive diagnostic tools used to detect viral or bacterial DNA in a sample is quantitative real-time polymerase chain reaction (qPCR). This technology has been tested rigorously in diagnosing hundreds of diseases and is generally more sensitive and specific compared to other diagnostic tests. Uhl et al. analyzed qPCR detection of GAS vs. the RADT (compared to beta-hemolytic GAS culture, the reference standard), and demonstrated that qPCR was more sensitive than the RADT (93% vs. 55%, respectively) and both had comparable specificities (qPCR 98% vs. RADT 99%).

Although qPCR can be an accurate diagnostic tool, this technology has historically been costly, time-consuming, and has required specialized training to perform; therefore, it has not commonly been used as a diagnostic tool in outpatient clinics. Within the last decade, next-generation qPCR technology has emerged (i.e., smaller, faster, easier to operate and more cost effective), providing the potential to overcome traditional barriers to using qPCR for the diagnosis of common infections in outpatient health care facilities.

The above information disclosed in this Background section is only for enhancement of understanding of the background of the inventive concept, and, therefore, it may contain information that does not form the prior art that is already known in this country to a person of ordinary skill in the art.

SUMMARY

Exemplary embodiments provide a method for conducting a saliva-based qPCR molecular diagnostic test to rapidly detect strep throat infection. Saliva processing and qPCR protocols according to exemplary embodiments are able to detect strep throat infection with 100% sensitivity and 100% specificity in 22-26 minutes, thus saliva can be rapidly analyzed via qPCR for the accurate and inexpensive detection of strep throat.

Exemplary embodiments also provide a rapid chelating resin-based protocol to extract DNA from human saliva samples that may be used in the downstream qPCR amplification of group A *Streptococcus* DNA for the diagnosis of strep throat infection.

Additional aspects will be set forth in the detailed description which follows, and, in part, will be apparent from the disclosure, or may be learned by practice of the inventive concept.

According to exemplary embodiments, a method for processing a saliva sample for downstream DNA analysis includes: mixing the saliva sample with a chelating resin solution to form a mixture; incubating the mixture at a temperature of 120° C. or lower and duration of at least 1 minute, wherein the temperature and duration are inversely related; shaking the mixture before and after incubation for a period ranging from 0 seconds to 2 hours; separating the mixture into a supernatant and a sedimented chelating resin using either centrifugation or by allowing natural gravitational settling; and recovering the supernatant for subsequent analysis.

According to exemplary embodiments, a method for conducting a saliva-based quantitative polymerase chain reaction (qPCR) diagnostic test for detecting Group A *Streptococcus* in a saliva sample includes: mixing the saliva sample with a chelating resin solution at a concentration of 10% (weight/volume) to form a mixture; incubating the mixture at a temperature of 120° C. for 1 minute; shaking the mixture before and after incubation for a period of 5 seconds; separating the mixture into a supernatant and a sedimented chelating resin using centrifugation at a speed in a range from 2000 g to 2680 g for 5 seconds; recovering the supernatant; preparing a qPCR master mix comprising mixing: 10 μl of a PCR supermix comprising a dye; 0.4 μl of a forward primer targeting the *Streptococcal pyrogenic* exotoxin B (SpeB) gene, the forward primer having the nucleotide sequence 5'-AAAGTAGGCGGACATGCCTTTG-3' (SEQ ID NO: 1); 0.4 μl of a reverse primer targeting the *Streptococcal pyrogenic* exotoxin B (SpeB) gene, the reverse primer having the nucleotide sequence 5'-CAAGACGGAAGAAGCCGTCAG-3' (SEQ ID NO: 2); and 4.2 μl of at least one of molecular biology-grade, ultrapure, and DNAse/RNAse-free water; adding the supernatant to a qPCR tube containing the qPCR master mix; subjecting the contents of the qPCR tube to a fast-cycling qPCR program on a qPCR machine, the program comprising: an initial polymerase activation and DNA denaturation step at 95° C. for 30 seconds; and 40 cycles of denaturation at 95° C. for 4 seconds and annealing/extension at 67° C. for 18 seconds; and analyzing the results of the fast-cycling qPCR program to determine the presence or absence of Group A *Streptococcus* in the saliva sample.

The foregoing description and the following detailed description are exemplary and explanatory and are intended to provide further explanation of the claimed subject matter.

BRIEF DESCRIPTION OF THE DRAWINGS

The accompanying drawings, which are included to provide a further understanding of the inventive concept, and are incorporated in and constitute a part of this specification, illustrate exemplary embodiments of the inventive concept, and, together with the description, serve to explain principles of the inventive concept.

DETAILED DESCRIPTION

Figure 1:
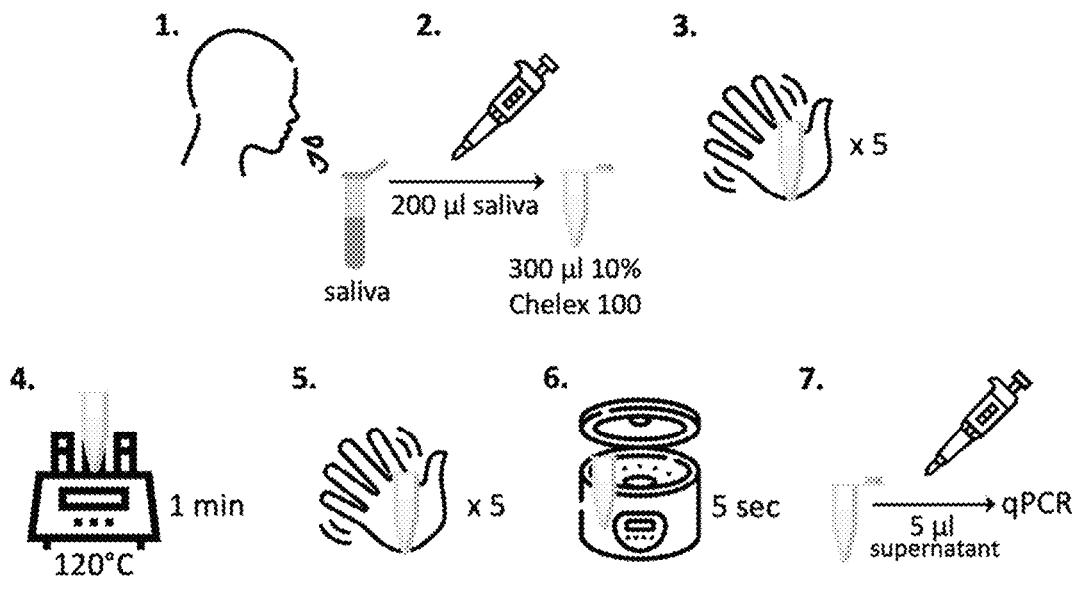
FIG. 1 is a chart showing a two-minute chelating resin-based DNA extraction protocol for saliva samples according to an exemplary embodiment.

In the following description, for the purposes of explanation, numerous specific details are set forth in order to provide a thorough understanding of various exemplary embodiments. It is apparent, however, that various exemplary embodiments may be practiced without these specific details or with one or more equivalent arrangements. This disclosure may be embodied in different forms and should not be construed as limited to the exemplary embodiments set forth herein. Rather, these exemplary embodiments are provided so that this disclosure will be thorough and complete, and will fully convey the scope of the disclosure to those skilled in the art.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

The term "at least one of" is intended to include the meaning of "at least one selected from" for the purpose of its meaning and interpretation. For example, "at least one of A and B" may be understood to mean "A, B, or A and B." When preceding a list of elements, the term, "at least one of," modifies the entire list of elements and does not modify the individual elements of the list.

It will be understood that, although the terms first, second, etc., may be used herein to describe various elements, these elements should not be limited by these terms. These terms are only used to distinguish one element from another element. For example, a first element may be referred to as a second element, and similarly, a second element may be referred to as a first element without departing from the scope of the disclosure.

"About", "approximately", or "substantially" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" may mean within one or more standard deviations, or within ±20%, 10%, or 5% of the stated value.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and will not be interpreted in an idealized or overly formal sense, unless expressly so defined herein.

Exemplary embodiments establish a new low-cost, accurate ST diagnostic test (hereinafter, the "test" according to exemplary embodiments may variously be referred to as "protocol" or "tool"). Exemplary embodiments disclose a diagnostic test for ST relying solely on saliva samples and use of a low-cost, rapid qPCR system as a diagnostic tool.

Saliva sample collection is inexpensive and non-invasive; however, saliva is an under-utilized tool in diagnosing disease and its collection is not standardized. GAS can be detected via qPCR in the saliva of infected patients according to other protocols, but these protocols may be lengthy, expensive and require specialized training to carry out the diagnostic tests. Additionally, DNA purity may be low in samples extracted from saliva, but low DNA purity does not inhibit qPCR amplification of Group A *Streptococcus* virus DNA using the diagnostic test according to exemplary embodiments.

Exemplary embodiments disclose a chelating resin (such as Chelex™ 100)-based DNA extraction technique, and a fast-qPCR protocol (such as Open qPCR™; 40 cycles in 20 min) for the accurate, rapid and inexpensive detection of ST using saliva samples (compared to traditional testing using a throat swab-collected sample). Exemplary embodiments disclose a high-accuracy rapid chelating resin protocol for amplifying Group A *Streptococcus* DNA from saliva samples using qPCR. The DNA extraction protocol according to exemplary embodiments can be implemented to isolate DNA for the rapid identification of bacterial and viral DNA targets.

DNA extraction and purification protocols provide a critical first step in the analysis, quantification, sequencing, or engineering of DNA in a biological sample. DNA extraction protocols may involve a form of cell lysis followed by the clearing cellular debris, denaturation of DNA, and inhibition of nucleases. Additional steps may be taken to purify the DNA, such as DNA precipitation or binding, washing, and elution. DNA extraction and purification protocols may range in complexity based on the steps and reagents involved and the desired downstream research aim. Common DNA extraction methods may involve using silica matrices, phenol-chloroform, SDS-proteinase K, salting-out, cetyltrimethylammonium bromide extraction, magnetic beads, cellulose-based paper, or chelating resins.

Chelating resin functions by binding divalent metal ions to inhibit nucleases in a sample. This chelating resin DNA extraction method is distinct from other DNA extraction techniques in that it is a simple, fast, and inexpensive way to isolate DNA from samples. However, this method may produce samples that may be contaminated with molecules other than DNA.

A microvolume UV-visible spectrophotometer can be used to measure the purity of DNA in a sample by assessing the ratio of absorbance at 230, 260, and 280 nm. Pure DNA samples exhibit a 260/280 ratio range of 1.7-2.0 and a 260/230 ratio range of 2.0-2.2. Lower ratios indicate a sample may be contaminated with phenol, proteins, carbohydrates, or other molecules. A standard chelating resin DNA extraction protocol may not include DNA purification steps, but longer, more complex chelating resin protocols can be used to fully purify DNA from a sample and increase overall DNA yield.

High DNA purity may be critical for downstream applications such as DNA quantification, genomic sequencing and genetic engineering. However, not all downstream applications require DNA samples to be free of impurities, and in such instances, a standard DNA extraction protocol may be sufficient.

Exemplary embodiments disclose a method of conducting a saliva-based qPCR diagnostic test to rapidly detect strep throat infection, as shown in FIG. 1, FIG. 2A, FIG. 2B, FIG. 3, FIG. 4, and FIG. 5. According to the present exemplary embodiment, to prepare a 10% (weight/volume) chelating resin solution, a user first measures 1 gram of chelating resin and places it in a sterile 15 ml tube. Next, molecular biology-grade water is added to the tube to achieve a final chelating resin solution volume of 10 ml. This solution should be stored at room temperature (20-25° C.). For sample processing, the user begins by preheating a heat block to 120° C. and allowing it to stabilize. The user then mixes the 10% chelating resin solution by inverting the 15 ml tube five times. Then, the user transfers 300 μl of the chelating resin solution into a sterile 1.5 ml tube using a pipette.

As shown in FIG. 1, to extract DNA from a saliva sample according to the present exemplary embodiment, a user starts by collecting the saliva sample in a sterile 5 ml snap-cap or centrifuge tube (Step 1). The user then pipettes 200 μl of the saliva sample into the 1.5 ml tube containing the chelating resin solution (Step 2). The user secures the cap on the tube and shakes it five times to ensure thorough mixing (Step 3), then places the tube in the preheated heat block at 120° C. for one minute (Step 4). After heating, the user removes the tube, avoiding direct contact with the heat block, and shakes it another five times (Step 5). Next, the user spins the tube in a mini-centrifuge for 5 seconds at a maximum speed of 2000-2680 g to form a supernatant (Step 6). Finally, the user opens the tube and extracts 5 μl of the supernatant, which can then be used for downstream qPCR analysis (Step 7).

According to the present exemplary embodiment, a saliva sample can be collected through any of the following methods. According to a spitting method, participants can spit (gently or forcefully) into any style or any size collection device, container or tube. Spitting into the collection device can be carried out with or without the use of a saliva collection funnel, saliva collection straw, or any similar tool that directs saliva into a collection device, container or tube. According to a passive drooling method, participants can allow saliva to pool in the mouth and then passively drool the saliva into any style or any size collection device, container or tube. Passive drooling into the collection device can be carried out with or without the use of a saliva collection funnel, saliva collection straw, or any similar tool that directs saliva into a collection device, container or tube. According to a suction method, any style suction device that draws up liquid can be used to collect saliva from a participant into any style or any size collection device, container or tube. According to exemplary embodiments, saliva samples are not collected using a general collection method such as absorption via a cotton swab or cotton roll, and samples do not undergo a mechanical filtration process using a plunger or porous filter for size-based particulate isolation. According to exemplary embodiments, saliva samples are not filtered.

A saliva processing protocol according to the present exemplary embodiment is described below. However, saliva processing protocols with varying solution percentages and sample or reagent volumes that deviate from the present exemplary embodiment can be used. According to the present exemplary embodiment, a saliva sample can be immediately run through a saliva processing protocol, or can be stored at any temperature ranging from –80° C. to 27° C. and subsequently run through a saliva processing protocol.

First, 300 µl of a 10% chelating resin solution (containing chelating resin diluted in any form of molecular grade, ultrapure or DNAse/RNAse-free water) is mixed with 200 µl of the saliva sample. The chelating resin solution can be added directly to the saliva sample or the saliva sample can be added directly to the chelating resin solution via pipetting, inversion of a tube containing the chelating resin solution into the saliva sample, or any other transfer method to combine the chelating resin and saliva sample. The saliva and chelating resin mixture can then be inverted, shaken, agitated or mixed by hand or by using a machine, tool, or product to invert, shake, agitate or mix (collectively generally referred to as "shaking") the saliva and chelating resin mixture. According to the present exemplary embodiment, the saliva and chelating resin mixture is shaken for 5 seconds, the but shaking can take place for any period of time, for example from 0 seconds to 2 hours.

According to the present exemplary embodiment, the saliva and chelating resin mixture is incubated at 120° C. for 1 minute. A longer incubation at lower temperatures can be carried out (e.g. 110° C. for 5 minutes, 100° C. for 10 minutes, 90° C. for 15 minutes, and even lower temperatures for longer durations). Any tool, device, or procedure can be utilized to incubate the sample, such as a heat block, water bath, incubating device, microwave, oven, heat gun, or other such heating device.

The incubated saliva and chelating resin mixture is then inverted, shaken, agitated or mixed by hand or by using a machine, tool, or product to invert, shake, agitate or mix the solution. According to the present exemplary embodiment, the saliva and chelating resin mixture is shaken for 5 seconds, the but shaking can take place for any period of time, for example from 0 seconds to 2 hours.

According to the present exemplary embodiment, the incubated saliva and chelating resin mixture is then placed in any size centrifuge to spin the contents of the mixture down at a speed of 2000-2680 g for 5 seconds. The user can spin the incubated mixture down at lower speeds with longer spin times. Alternatively, the saliva and chelating resin mixture can be allowed to settle and separate over any period of time naturally using gravity alone. Mechanical (centrifugation or other separating device) or natural (gravitational) separation of the saliva and chelating resin mixture allows for the separation of the contents of the mixture. The chelating resin settles on the bottom of the sample and the top liquid of the sample (supernatant) remains on the top of the sample.

The supernatant liquid at the top of the sample can be removed and placed into a separate tube containing reagents to run a qPCR reaction. 5 µl of the supernatant is transferred into the tube with prepared qPCR master mix, as described below. However, other volumes of supernatant can be removed and transferred to the qPCR tube. Any tool, device, or method can be used to remove supernatant from the top of the sample and place it into a qPCR tube.

Compared to longer, more complex, and more expensive DNA purification methods, the protocol according to the present exemplary embodiment produces samples with low 260/280 ratios (average 0.91, SD 0.14) and low 260/230 ratios (average 0.27, SD 0.05). Low 260/280 and 260/230 ratios indicate a sample may be contaminated with phenol, proteins and/or carbohydrates. The protocol according to the present exemplary embodiment does not use phenol, so this would not be a contaminating compound, but protein and carbohydrates may be found in saliva since these macromolecules are secreted from salivary glands. Additionally, food particles containing protein and carbohydrate macromolecules may also be present in saliva samples.

Protein contamination of DNA samples can inhibit qPCR analysis, whether that be through protease activity or other unknown mechanisms. Additionally, complex carbohydrates such as polysaccharides may inhibit qPCR amplification of DNA. However, according to exemplary embodiments, protein and carbohydrate contaminants present in DNA samples produce no significant inhibitory effect on downstream qPCR analysis (see Table 2 below).

In the protocol according to the present exemplary embodiment, samples undergo a 1-minute, 120° C. boiling step which results in the denaturation of proteins and degradation of polysaccharides in the sample. The denatured, biologically inactive proteins may no longer inhibit qPCR amplification of DNA. High temperatures may degrade polysaccharides into smaller oligo-and monosaccharides, which may enhance PCR amplification of DNA.

According to the present exemplary embodiment, a qPCR master mix was assembled using the following reagents in the following volumes, but other reagents and volumes can be used to assemble a qPCR master mix. To prepare a 15 µl strep throat diagnostic qPCR master mix, a user pipettes the following reagents into a sterile 100 or 200 µl qPCR tube: 10 µl of a PCR supermix such as 2×SSOAdvanced Universal SYBR® Green Supermix; 0.4 µl of forward GAS primer targeting the *Streptococcal pyrogenic* exotoxin B (SpeB) gene with the sequence 5'-AAAGTAGGCGGA-CATGCCTTTG-3' (SEQ ID NO: 1), 0.4 µl of reverse GAS primer targeting the same gene with the sequence 5'-CAA-GACGGAAGAAGCCGTCAG-3' (SEQ ID NO: 2), and 4.2 µl of molecular biology-grade water, ultrapure, or DNAse/RNAse-free water. The qPCR master mix according to the present exemplary embodiment remains stable when stored at –20° C. However, to prepare a qPCR master mix according to exemplary embodiments, any volume of any kind of fluorescent dye generated by any manufacturer used in nucleic acid amplification reactions, any volume of any other primer used to detect *Streptococcus pyogenes* in nucleic acid amplification reactions, and any volume of water may be used. The reagents for the qPCR master mix can be transferred into any size tube that fits into any qPCR machine.

Next, for the qPCR protocol according to the present exemplary embodiment, a user adds 5 µl of the supernatant obtained from the DNA extraction step (described above) to the qPCR tube containing 15 µl of the prepared qPCR master mix. The user then uses a fast-cycling qPCR machine to run the following program: an initial polymerase activation/DNA denaturation step at 95° C. for 30 seconds, followed by 40 cycles of denaturation at 95° C. for 4 seconds and annealing/extension at 67° C. for 18 seconds. Any qPCR machine can be used for sample analysis according to exemplary embodiments. Further, qPCR protocols can be used that deviate from the one described above with varying temperatures, timing, and cycle numbers.

Experimental Results

DNA extraction from saliva samples. Various DNA purification protocols were compared and tested in the process of developing a method of low-cost, simple DNA extraction according to exemplary embodiments. Compared to complex, expensive protocols used by standard DNA purification kits, and long protocols involving chelating resin, a chelating resin-based DNA extraction protocol for saliva samples that involves six simple steps, takes 2 minutes to perform, and costs approximately $0.07 per sample to process was developed according to exemplary embodiments.

Figure 2A:
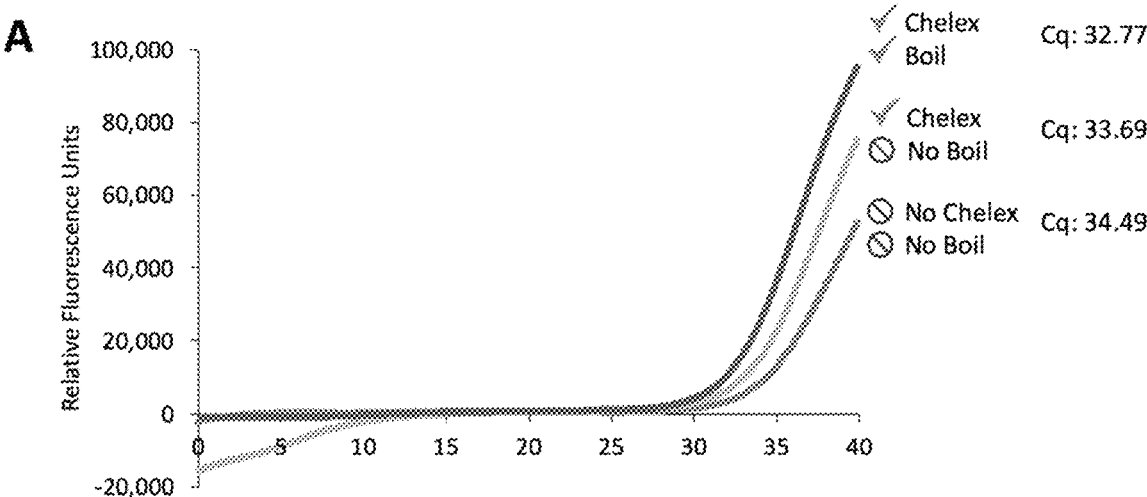
FIG. 2A and FIG. 2B are charts showing a comparison of variables for a process of qPCR detection of GAS DNA according to the exemplary embodiment.
Figure 2B:
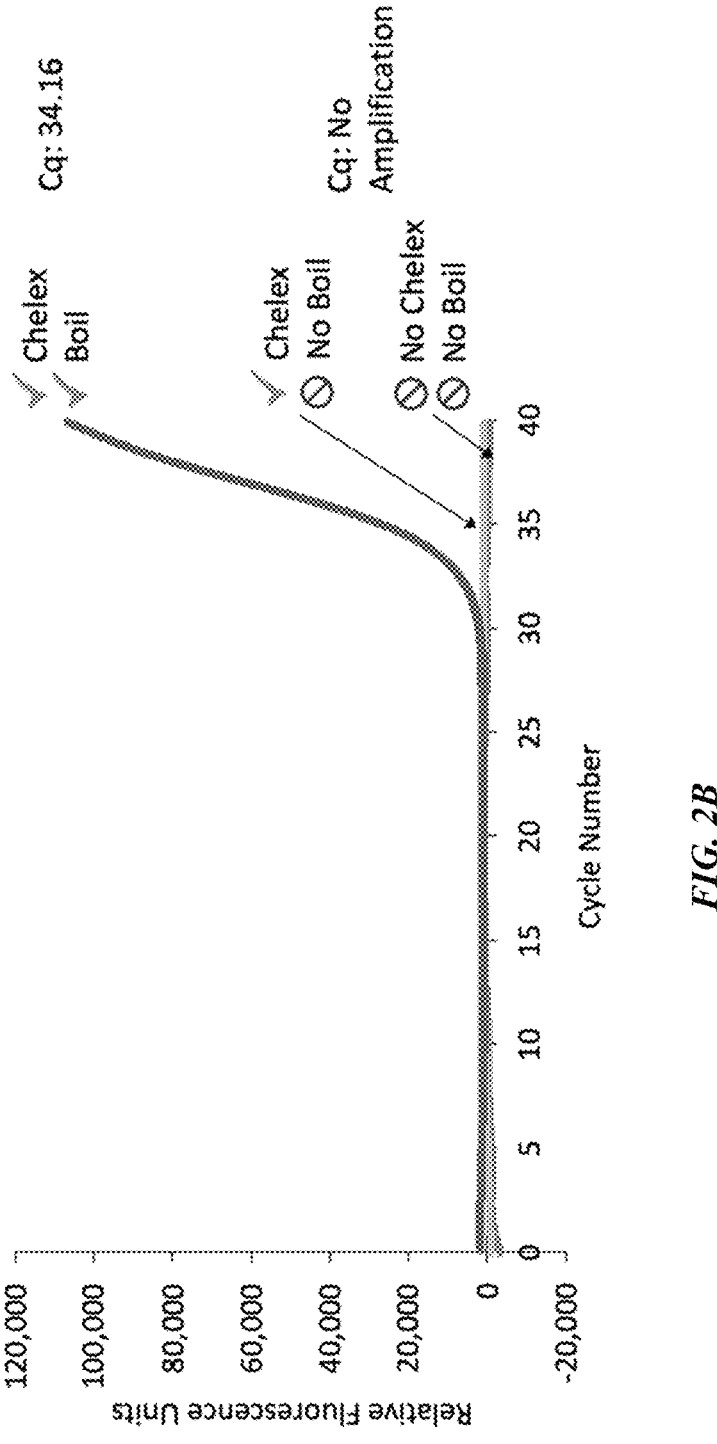

A multitude of variables were tested, as shown in Table 1 below, FIG. 2A and FIG. 2B: processing samples with or without 10% chelating resin, a boiling step, or a cell lysis buffer; vortexing vs. hand mixing; boiling at 100° C. for 20 minutes vs. a higher temperature for a shorter period of time; and shorter spin times in the centrifuge vs. no centrifuge spinning. FIG. 2A and FIG. 2B demonstrate the importance of adding 10% chelating resin and a boiling step (either 20 minutes at 100° C. or 1 minute at 120° C.) for sufficient DNA extraction and GAS DNA amplification via qPCR. Not only did addition of 10% chelating resin plus a boiling step allow for a more robust detection of GAS DNA (i.e., lower quantification cycle (Cq)), but it was a critical step for the detection of GAS DNA in some samples.

Table 1: Protocol Testing

To develop the qPCR diagnostic protocol for ST according to the present exemplary embodiment, various qPCR protocols and GAS primers were tested. First, a standard

| DNA Extraction Testing | |
| --- | --- |
| | Average Cq |
| Vortexing vs. Shaking by Hand | |
| No vortexing or shaking by hand | 35.25 |
| Shaking by hand once | 37.29 |
| Shaking by hand twice | 32.61 |
| Vortexing twice | 33.29 |
| Sample Boiling Temperature and Time | |
| 100° C. for 10 min | 33.38 |
| 100° C. for 5 min | 34.03 |
| 110° C. for 5 min | 32.13 |
| 120° C. for 3 min | 28.30 |
| 120° C. for 2 min | 31.96 |
| 120° C. for 1 min | 30.50 |
| 120° C. for 45 sec | 36.03 |
| 120° C. for 30 sec | 34.61 |

| Length of Centrifuge Spin | Pellet formed |
| --- | --- |
| 5 s | YES |
| 10 s | YES |
| 15 s | YES |
| 20 s | YES |

| qPCR Protocol Testing Protocol Speed[a] | Average Cq |
| --- | --- |
| Standard Protocol | 33.29 |
| Fast Protocol 1 | 34.41 |
| Fast Protocol 2 | 38.10 |
| Fast Protocol 3 | 36.07 |

[a]A total of 20 fast protocols were tested. Data from three fast protocols are displayed here. Bolded, italicized text indicates steps that were selected for the final protocol. Cq, quantification cycle.

53+ minute qPCR protocol was run (95° C. for 10 minutes followed by 40 cycles of 95° C. for 15 seconds, 55° C. for 22 seconds, 72° C. for 30 seconds) on a CFX Connect™ Real-Time PCR machine. Three different GAS primers specific for the dnaseB gene (1 primer set) and speB gene (2 primer sets) were tested using DNA extracted from participant saliva. One speB primer set displayed the highest sensitivity and specificity for GAS detection in all samples and was used hereafter in the present exemplary embodiment.

In order to amplify GAS DNA with speed and accuracy according to exemplary embodiments, samples underwent repeated testing on both the CFX Connect™ Real-Time PCR and Open qPCR™ machines under various protocols with slightly altered denaturation, annealing and extension times. According to the present exemplary embodiment, the following qPCR protocol was identified as the most effective: initial polymerase activation/DNA denaturation step at 95° C. for 30 seconds followed by 40 cycles of denaturation at 95° C. for 4 seconds and annealing/extension at 67° C. for 18 seconds. The saliva-based qPCR ST diagnostic test according to the present exemplary embodiment can be run significantly faster than a standard qPCR test, with positive results developing at 20 minutes and negative results confirmed by 24 minutes.

For diagnosis according to the present exemplary embodiment, the presence of an upward sloping line and/or a provided cycle threshold number during a qPCR diagnostic readout signifies that GAS DNA is present in the sample, indicating a positive result for strep throat. A flat line and/or the lack of a cycle threshold number or a cycle threshold number of zero or near zero signifies that GAS DNA is not present in the sample, indicating a negative result for strep throat.

Figure 3:
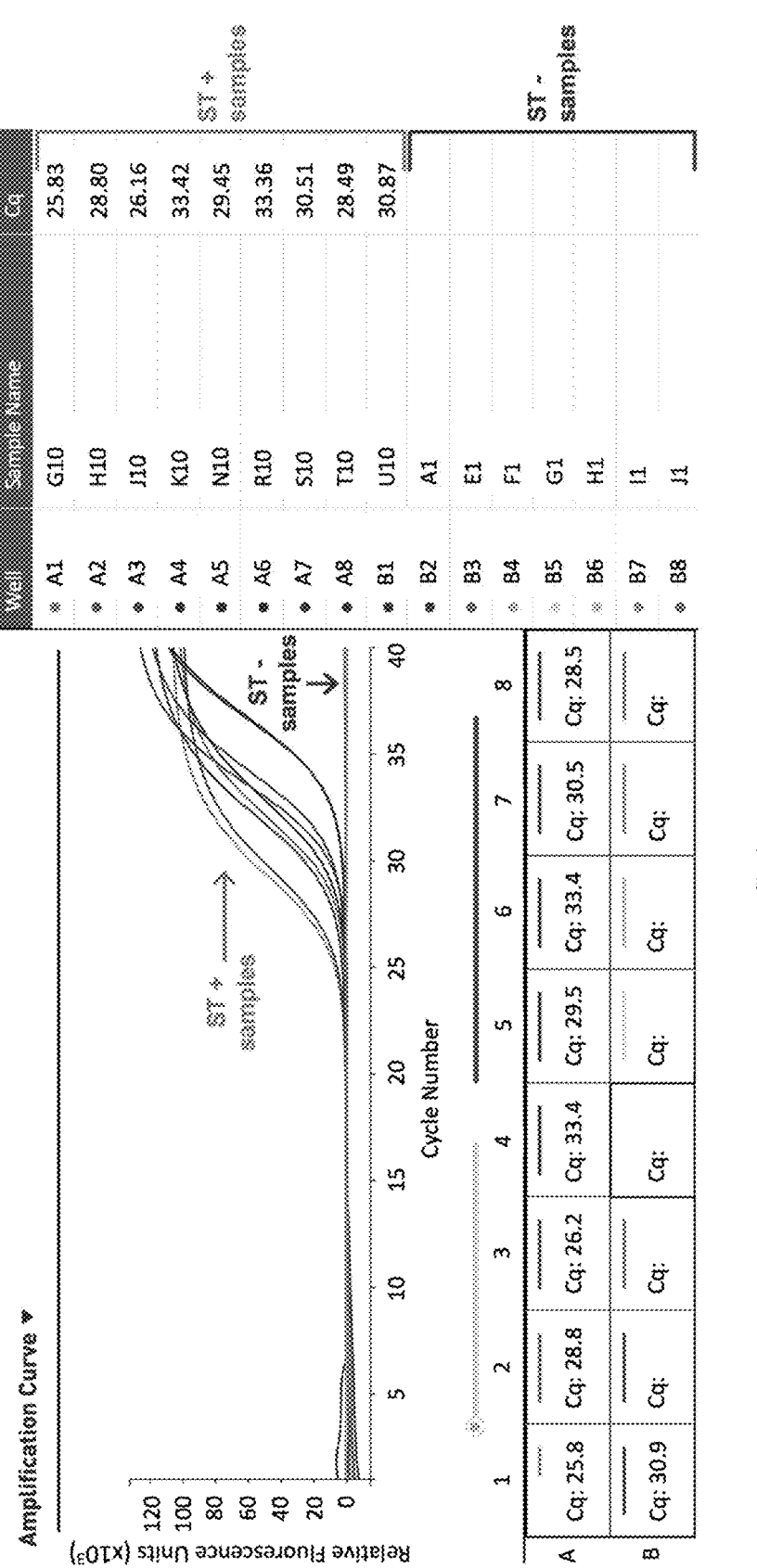
FIG. 3 is a qPCR diagnostic readout according to the exemplary embodiment.

FIG. 3 shows a qPCR diagnostic readout. Samples in wells A1-B1 were strep throat positive (ST+) samples that displayed GAS DNA amplification, indicated by an upward sloping line and a calculated quantification cycle (Cq) value. Samples in wells B2-B8 were ST negative (ST−) samples that displayed no GAS DNA amplification, indicated by a flat line and no calculated Cq value.

As shown in Table 2 below, results from the saliva-based qPCR ST diagnostic test according to the present exemplary embodiment were compared to reference standard beta-hemolytic GAS culture results when calculating the presently disclosed statistics. Further, as shown in Table 3 below, comparative example results from a saliva-based self-use (home) ST diagnostic test (i.e., data gathered on a different device using a different saliva collection technique and a different processing and analysis method than exemplary embodiments) are shown. According to the present exemplary embodiment, the saliva-based qPCR ST diagnostic test displayed 100% sensitivity and 100% specificity, with no false positive or false negative test results compared to a standard beta-hemolytic GAS culture. Conversely, the saliva-based home diagnostic test according to the comparative example displayed 88.23% sensitivity and 96.00% specificity, which contained false positive and false negative test results.

TABLE 2

| Saliva-based Open qPCR strep throat diagnostic test statistics. | | |
| --- | --- | --- |
| Statistic | Value | 95% CI |
| Sensitivity | 100.00% | 96.38% to 100.00% |
| Specificity | 100.00% | 96.38% to 100.00% |
| Disease Prevalence | 48.00% | |
| Positive Predictive Value[a] | 100.00% | 96.38% to 100.00% |
| Negative Predictive Value[a] | 100.00% | 96.38% to 100.00% |
| Accuracy[a] | 100.00% | 98.17% to 100.00% |

[a]Value is dependent on disease prevalence. CI, confidence interval.

TABLE 3

| (Comparative Example). | |
| --- | --- |
| Sensitivity | 88.23% |
| Specificity | 96.00% |
| NPV | 88.89% |
| PPV | 95.74% |

Sensitivity is the probability that a test result will be positive when a disease is present: Sensitivity=#True Positive/(#True Positive+#False Negative), and is expressed as a percentage. Specificity is the probability that a test result will be negative when a disease is not present: Specificity=#True Negative/(#True Negative+#False Positive), and is expressed as a percentage. 95% confidence intervals (CIs) are "exact" Clopper-Pearson CIs.

Disease Prevalence indicates disease prevalence in the study population: #Positive Beta-Hemolytic GAS Cultures/Total Study Population, and is expressed as a percentage. Positive Predictive Value ("PPV") is the probability that those with a positive test do have the disease: Positive Predictive Value=Sensitivity×Prevalence/ [(Sensitivity×Prevalence+(1−Specificity)×(1−Prevalence)], and is expressed as a percentage. Negative Predictive Value is the probability that those with a negative test do not have the disease: Negative Predictive Value ("NPV")=Specificity×(1−Prevalence)/[(1−Sensitivity)×Prevalence+Specificity×(1−Prevalence)], and is expressed as a percentage. Accuracy is the overall probability that a patient is correctly diagnosed: Sensitivity×Prevalence+Specificity×(1−Prevalence), and is expressed as a percentage.

Figure 4:
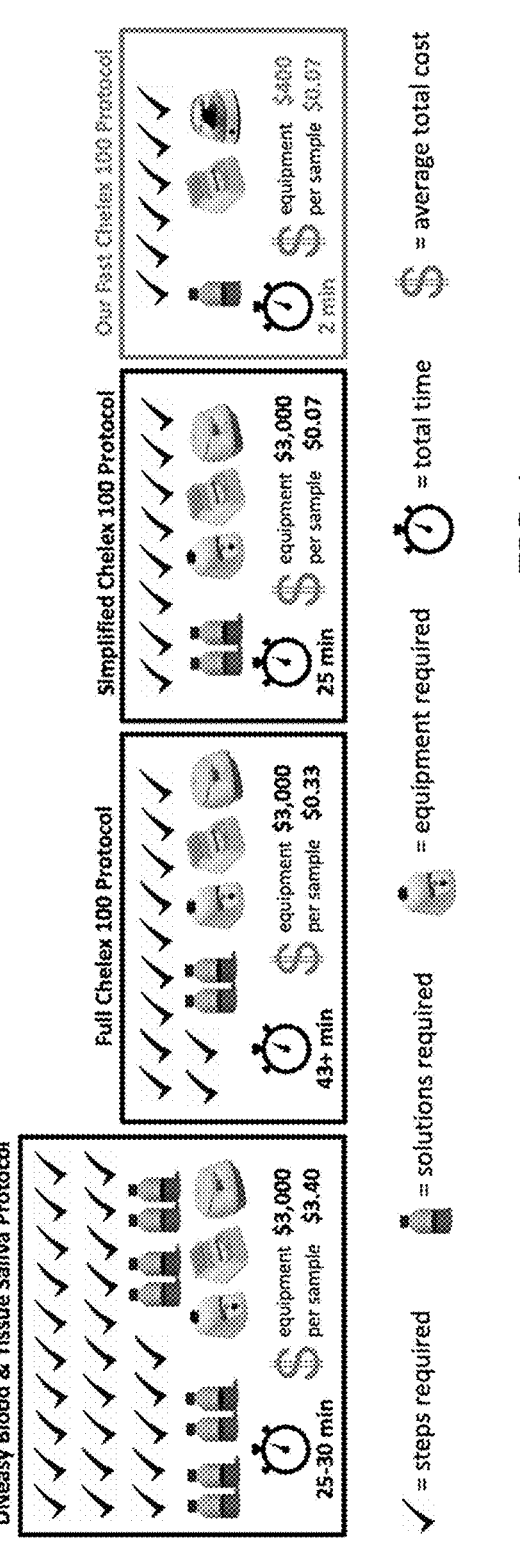
FIG. 4 is a chart showing a comparison of DNA extraction protocols.

Accordingly, as shown in FIG. 4, a simple chelating resin protocol can be used to quickly extract GAS DNA from saliva, and longer protocols are not required for effective downstream qPCR quantification of GAS DNA. Chelating resin was used in the present exemplary embodiment due to its low cost and ability to bind to multivalent metal ions to inhibit DNases from degrading DNA after the critical boiling step. Primers specific for the speB gene, when run through the qPCR protocol according to the present exemplary embodiment (40 cycles in 20 minutes), are capable of accurately diagnosing ST with 100% sensitivity and 100% specificity compared to reference standard diagnostics.

DNA yields resulting from the protocol according to the present exemplary embodiment varied, ranging from 39 ng/μl to 539 ng/μl with an average yield of 155.02 ng/μl and standard deviation of 126.17 (see Table 4 below). According to the present exemplary embodiment, UV-visible spectrophotometer 260/280 absorbance ratios ranged from 0.71-1.155 with an average ratio of 0.91, and 260/230 absorbance ratios ranged from 0.195-0.373 with an average ratio of 0.27. Table 4 displays UV-visible spectrophotometer data collected from supernatant samples at the completion of the DNA extraction protocol according to the present exemplary embodiment (n=15). Although additional purification steps may increase DNA yields, high DNA yields are not required for qPCR detection of bacterial DNA according to the present exemplary embodiment, and lower yields are sufficient to identify Group A *Streptococcus* DNA in saliva samples.

TABLE 4

| (Present Exemplary Embodiment). | | |
| --- | --- | --- |
| Quantification | Average | SD |
| DNA Yield (ng/μl) | 155.02 | 126.17 |
| 260/280 Ratio | 0.91 | 0.14 |
| 260/230 Ratio | 0.27 | 0.05 |

When a DNA yield measurement is taken, substantially all of the DNA present in the sample may be quantified. For a saliva sample, this may include DNA from anything that was present in the mouth or saliva at the time the sample was taken, and may include bacterial, viral, or human DNA. It is conventional thought that a high DNA yield (greater than 300 ng/μl) is required to successfully gather qPCR data. However, even with low DNA yields and impure DNA that is not free from contaminants, the diagnostic test according to exemplary embodiments can still successfully identify the presence or absence of GAS DNA in a sample. Thus, according to exemplary embodiments, highly accurate GAS detection is achieved even with samples having low DNA yields, as demonstrated by the Cq values of positive ST tests, as shown in the accompanying figures.

Figure 5:
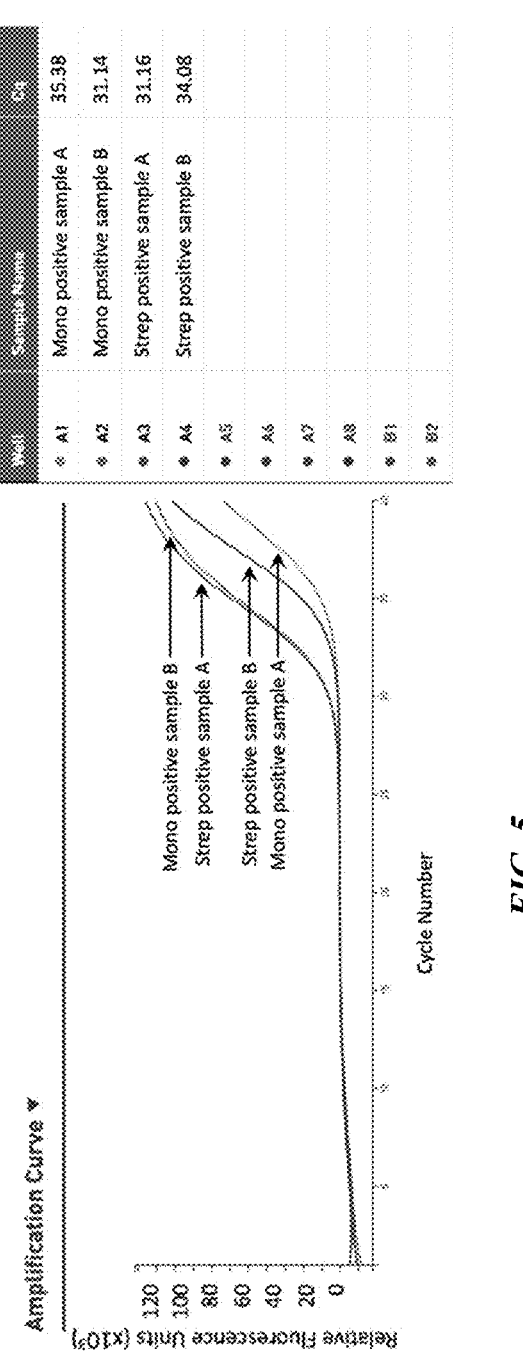
FIG. 5 is a qPCR diagnostic readout according to an exemplary embodiment.

Not only is saliva collection (as described above) less invasive than the standard throat swab, DNA in saliva samples can remain stable for months. Accordingly, the protocol according to exemplary embodiments may be extremely effective in diagnosing bacterial and viral illnesses via qPCR. FIG. 5 shows the amplification of Epstein-Barr virus, the causative agent of infectious mononucleosis ("mono"), in mono-positive saliva samples processed through the protocol according to the present exemplary embodiment. Amplification of Group A *Streptococcus* DNA was also detected in strep positive saliva samples.

No special qPCR training may be required to run the qPCR ST diagnostic test according to the present exemplary embodiment, and test results are easy to read. Following the one-time purchase of a qPCR machine, a heat block, and a mini centrifuge, samples can be processed and run for approximately $1.12 per sample. This is a fraction of the cost and time it would take to run qPCR diagnostics at an external lab or perform beta-hemolytic GAS culture. Additionally, the chelating resin solution and qPCR master mix can be prepared in advance and stored at 4° C. and −20° C., respectively, for up to at least 5 months. Preparing these reagents in advanced allows for saliva samples to be tested immediately as soon as they become available.

Although RADTs can provide results within a short time frame, they exhibit low sensitivity which may lead to inappropriate treatment for those who receive false negative results. The potential also exists that heath care providers, knowledgeable of this low sensitivity, may prescribe antibiotics even when a patient has a negative test result; this may account for the recorded overprescription of antibiotics in patients with pharyngitis. Although the qPCR ST diagnostic protocol according to the present exemplary embodiment may take slightly longer than RADTs to produce results, it can provide 100% sensitivity, 100% specificity and 100% accuracy in diagnosing ST.

The total cost of equipment required to run the qPCR ST diagnostic protocol according to the present exemplary embodiment was approximately $5,000, which included the purchase of an Open qPCR™ machine, heat block, and mini centrifuge. The total cost to run one saliva sample through the qPCR ST diagnostic protocol was approximately $1.12. This calculation includes the cost of test tubes, Chelex®

100, and SSO Advanced Universal SYBR® Green Supermix. Compared to the ST RADT, the qPCR ST diagnostic protocol according to the present exemplary embodiment is more sensitive, more specific and less expensive. Compared to beta-hemolytic GAS culture, the qPCR ST diagnostic protocol according to the present exemplary embodiment is less expensive, faster, and is equally as sensitive and specific as this reference standard.

Saliva-based qPCR diagnostic protocols according to exemplary embodiments yield rapid, accurate, cost-effective test results for ST, thus making it a suitable platform for outpatient health care facilities. Further, qPCR testing for saliva-based identification of other DNA and RNA-based infectious pathogens may be possible according to implementation of the qPCR diagnostic protocol according to exemplary embodiments.

Although certain exemplary embodiments and implementations have been described herein, other embodiments and modifications will be apparent from this description. Accordingly, the inventive concept is not limited to such embodiments, but rather to the broader scope of the presented claims and various obvious modifications and equivalent arrangements.

5. The method of claim 1, wherein 300 µl of the chelating resin solution is mixed with 200 µl of the saliva sample.

6. The method of claim 1, wherein separating the mixture into a supernatant and a sedimented chelating resin comprises allowing natural gravitational settling of the sedimented chelating resin.

7. The method of claim 1, wherein shaking the mixture before and/or after incubation is performed and comprises inversion, mechanical agitation, or hand shaking.

8. The method of claim 1, wherein incubating the mixture is performed using a heating device selected from the group consisting of a heat block, water bath, incubator, microwave, oven, and heat gun.

9. The method of claim 1, wherein the saliva sample is collected using a spitting method, a passive drooling method, or a suction method.

10. A method for detecting bacterial DNA in a saliva sample comprising:
    mixing the saliva sample with a chelating resin solution to form a mixture;
    incubating the mixture at a temperature of from 100° C. to 120° C. for a duration of from 30 seconds to 10 minutes, wherein the temperature and duration are inversely related;

What is claimed is:

1. A method for processing a saliva sample for subsequent bacterial DNA analysis, the method comprising:
    mixing the saliva sample with a chelating resin solution to form a mixture;
    incubating the mixture at a temperature of from 100° C. to 120° C. for a duration of from 30 seconds to 10 minutes, wherein the temperature and duration are inversely related;
    optionally shaking the mixture before and/or after incubation for a period up to 2 hours;
    separating the mixture into a supernatant and a sedimented chelating resin; and
    recovering the supernatant for subsequent bacterial DNA analysis.

2. The method of claim 1, wherein incubating the mixture is performed at a temperature of 120° C. for 1 minute.

3. The method of claim 2, wherein the mixture is respectively shaken for up to 5 seconds before and after incubating the mixture.

4. The method of claim 1, wherein the chelating resin solution comprises a chelating resin diluted in at least one of molecular grade water, ultrapure water, and DNAse/RNAse-free water, and the chelating resin is present in the chelating resin solution at a concentration of 10% (weight/volume).

separating the mixture into a supernatant and a sedimented chelating resin; and
subjecting the supernatant to quantitative real-time polymerase chain reaction (qPCR) analysis to determine whether bacterial DNA is present in the supernatant, wherein incubating the mixture inactivates sufficient proteins present in the mixture such that qPCR analysis of the supernatant is not inhibited.

11. The method of claim 10, wherein the bacterial DNA is Group A *Streptococcus* DNA.

12. The method of claim 11, wherein the qPCR analysis comprises mixing the supernatant with a diagnostic master mix comprising a forward primer targeting the Streptococcal pyrogenic exotoxin B (SpeB) gene, the forward primer having the nucleotide sequence 5'-AAAGTAGGCGGA-CATGCCTTTG-3' (SEQ ID NO: 1); and a reverse primer targeting the *Streptococcal pyrogenic* exotoxin B (SpeB) gene, the reverse primer having the nucleotide sequence 5'-CAAGACGGAAGAAGCCGTCAG-3' (SEQ ID NO: 2).

13. The method of claim 12, wherein the qPCR analysis comprises annealing/extension at about 67° C.

14. The method of claim 12, wherein the diagnostic master mix further comprises a PCR supermix comprising at least one dye and at least one of molecular biology-grade water, ultrapure water, and DNAse/RNAse-free water.

15. The method of claim 10, wherein separating the mixture into a supernatant and a sedimented chelating resin comprises allowing natural gravitational settling of the sedimented chelating resin.

16. The method of claim 10, wherein incubating the mixture occurs at a temperature of 120° C. for 1 minute.

17. The method of claim 11, wherein incubating the mixture occurs at a temperature of 120° C. for 1 minute.

18. The method of claim 15, wherein incubating the mixture occurs at a temperature of 120° C. for 1 minute.

19. The method of claim 11, wherein separating the mixture into a supernatant and a sedimented chelating resin comprises allowing natural gravitational settling of the sedimented chelating resin.

20. The method of claim 10, wherein 300 μl of the chelating resin solution is mixed with 200 μl of the saliva sample.

\* \* \* \* \*